(12) United States Patent
Gentry Mullins

(10) Patent No.: US 6,392,061 B1
(45) Date of Patent: May 21, 2002

(54) PROCESS FOR MAKING (2S, 3S, 5S) OXETANONE DERIVATIVES

(75) Inventor: John Jason Gentry Mullins, San Francisco, CA (US)

(73) Assignee: Zpro Chemical, Inc., Dover, DE (US)

( * ) Notice: Subject to any disclaimer, the term of this patent is extended or adjusted under 35 U.S.C. 154(b) by 0 days.

(21) Appl. No.: 09/840,329

(22) Filed: Apr. 23, 2001

Related U.S. Application Data

(62) Division of application No. 09/688,553, filed on Oct. 16, 2000, now abandoned.

(51) Int. Cl.[7] .................... C07D 309/06; C07D 69/66
(52) U.S. Cl. ................ 549/420; 549/423; 549/510; 549/511; 560/189
(58) Field of Search ................ 560/189; 549/420, 549/423, 510, 511

(56) References Cited

U.S. PATENT DOCUMENTS 5,246,960 A * 9/1993 Barbier et al. ............... 514/422
5,466,708 A * 11/1995 Derungs et al. ............ 514/449

\* cited by examiner

*Primary Examiner*—Ba K. Trinh
(74) *Attorney, Agent, or Firm*—Robert Lev

(57) ABSTRACT

This invention relates to novel processes for making (2S, 3S, 5S) oxetanone derivative lipase inhibitor compounds and intermediates therefor, which processes for producing such derivatives that are useful as lipase inhibitors are capable of being scaled to commercial quantities. Further the invention relates to processes for producing salts and for producing pharmaceutical compositions compounds comprising at least one such oxetanone derivative or salt, as well as methods for using such compounds and compositions for inhibiting lipases.

4 Claims, No Drawings

PROCESS FOR MAKING (2S, 3S, 5S) OXETANONE DERIVATIVES

This application is a divisional of application Ser. No. 09/688,553 file Oct. 16, 2000 now abandoned.

FIELD OF THE INVENTION

This invention relates to novel oxetanone derivative compounds and processes for producing such derivatives which are useful as lipase inhibitors. Further the invention relates to processes for producing salts and for producing pharmaceutical compositions compounds comprising at least one such oxetanone derivative or salt, as well as methods for using such compounds and compositions for inhibiting lipases. In one aspect the invention relates to lipase inhibitors which include on the same molecule an oxetanone derivative portion capable of inhibiting a lipase and a non-absorbable moiety such a polysaccharide, which are covalently linked or are in the form of a salt. In a preferred aspect of the invention the non-absorbable moiety is lipophilic and will associate with oils or fats. An absorbable oxetanone lipase inhibitor may be rendered non-absorbable by covalent linking it directly or indirectly to a non-absorbable moiety and thereby producing a novel non-absorbable lipase inhibitor.

BACKGROUND OF THE INVENTION

Some lipase-inhibiting oxetanones and intermediates for making them are well known. See for example, U.S. Pat. Nos. 5,931,463, 5,175,186, 4.189,438 and 4,202,824. However, there is a need for improved processes for making oxetanones in commercial quantities that are have low toxicity and are essentially not absorbable by the digestive system of mammals such as dogs, cats, non-human primates and human primates.

Lipase inhibitors such as esterastin (2S, 3S, 5S) 3,5-hydroxy-2-hexadeca-7,10-dienoic 1,3-lactone), tetrahydroesterastin (2S, 3S, 5S) 3,5-di-hydroxy-2-hexylhexadecanoic 1,3-lactone, and the like (see U.S. Pat. No. 4,189,438), are well-known as lipase inhibitors and are useful as pancreatic cholesterol esterase inhibitors. While these lipase inhibitor can be obtained by cultivating microbes as described in U.S. Pat. No. 4,189,438, it is believed that examples of successful synthetic procedures for effectively making such compounds in commercially acceptable quantities from intermediates other than those obtained from microbes have not been described in the literature.

Further, esterastin and tetrahydroesterastin are excluded by proviso from the claims of the U.S. Pat. No. 5,175,186, which relates to a synthetic method for making certain analogs of esterastin and tetrahydroesteratin. The specification of that document does not illustrate the direct production of esterastin or tetrahydroesteratin or other (5S) analogs before the 2S, 3S oxetanone (lactone) ring structure is formed. Further page 6, lines 21–44, of the 5,175,186 patent points to an asymetrical hydrogenation synthesis step, which makes obtaining (2S, 3S, 5S) analog compounds before the direct closure of the oxetanone ring problematic. On page 6, when an intermediate compound having the 5 hydroxyl group in the R configuration (6R intermediate), is selectively hydrogenated only the (3S, 4S, 6R) intermediates result, which convert to a final compound having a 2S, 3S, 5R configuration. Likewise, when a only a 6S intermediate is used the (3R, 4R, 6S) hydrogenation intermediates result. The 5,175,186 patent does not illustrate a feasible and efficient solution for resolving such a synthetic difficulty prior to closure of the oxetanone ring.

Accordingly, there is a need in the art for an improved commercial process for efficiently making tetrahydroesterastin and its (2S, 3S, 5S) analogs in a enantiomeric excess of greater than 70% by the use of 2S, 3S, 5S intermediate compounds which are formed prior to the formation of the oxetanone ring structure.

SUMMARY OF THE INVENTION

In one aspect the present invention relates to novel process for making in at least 70% enantiomeric purity a (3S, 4S, 6S) oxetanone compound of the formula (I),:

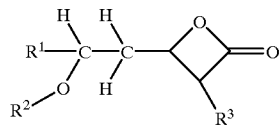

or a salt thereof
wherein:
  $R^1$ and $R^3$ are each independently a $C_1$ to $C_{18}$ straight or branched alkyl hydrocarbon chain, and
  $R^2$ is hydrogen or an alcohol protecting group $R^{10}$, wherein $R^{10}$ can be replaced by a hydrogen atom via ester hydrolysis or hydrogenation ether degradation, comprising the steps of:
    (a) selectively hydrogenating a composition comprising a compound which is a member selected from the group consisting of (6R) tetrahydro-2H-pyran-2-one compound of formula (II) and (6R) 5,6-dihydro-2H-pyran-2,4-dione of formula (IIa):

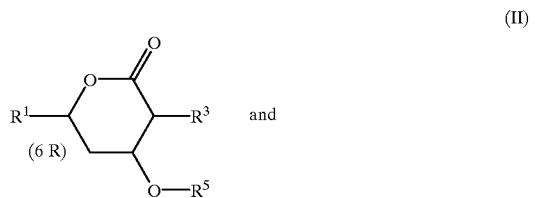

wherein
  $R^5$ is hydrogen or an alcohol protecting group, which can be replaced by a hydrogen atom via hydrogenation, and $R^1$ and $R^3$ are defined as in formula (I), by hydrogenating the compound of formula II with a hydrogenation catalyst selected from the group consisting of $PtO_2$, Raney Nichel and the like, and exchanging hydrogen atoms at the 3 and 4 ring positions or oxidizing the 4-oxo group to provide a (3S, 4S, 6R) 4-hydroxy-tetrahydro-2H-pyran-2-one compound of the formula (III):

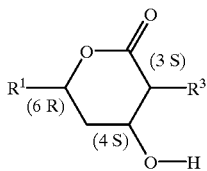

wherein $R^1$ and $R^3$ are defined as in formula (I);

(b) re-protecting the 4-hydroxy group of the compound of formula (II) produced in (a) with an ether protecting group $R^6$, which can be replaced by a hydrogen atom via ester hydrolysis or hydrogenation ether degradation, opening the lactone ring and esterifying the resulting free acid group to provide a (2S, 3S, 5R) [$R^7$] 2-[$R^3$]-3-[$R^{6-}$oxy]-5-[hydroxy, $R^1$] pentanoic acid ester compound of the formula (IV):

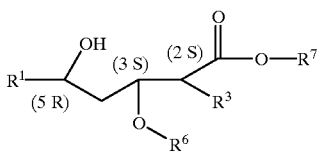

wherein $R^1$ and $R^3$ are defined as in formula (I), $R^6$ is an alcohol protecting group, which can be replaced by a hydrogen atom via ester hydrolysis or hydrogenation ether degradation, and $R^7$ is an ester group which can be removed by base or acid hydrolysis, or by hydrogenation;

(c) inverting the chirality of the 5-hydroxy group of the compound of formula (IV) produced in step (b), wherein the inversion comprises a step which is a member selected from the group consisting of
  (i) a Mitsunobu reaction,
  (ii) esterifying the 5-hydroxy group to a carboxylic acid ester such as the trichloroacetic acid ester, and the like, and hydrolyzing the resultant ester in a water ether solvent such as 3:1 $H_2O$/ dioxane, and
  (iii) esterifying the 5-hydroxy group to a sulfonic acid ester, such as p-toluene sulfonic acid ester and the like, and reacting the ester with an excess of an organic acid salt selected from the group consising of potassium acetate, sodium acetate, tetraethylammonium acetate, and the like, to provide an ester exchange with the organic acid, wherein the free inverted (5S) 5-hydroxy group of (i) and (ii) is esterified with a hydroxy protecting group $R^{10}$ which can be which can be replaced by a hydrogen atom via ester hydrolysis or hydrogenation ether degradation, to provide a compound of the formula (V):

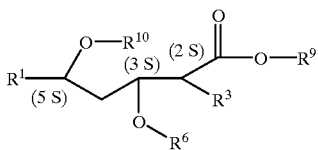

wherein $R^1$ and $R^3$ are defined as in formula (I), $R^6$ is an alcohol protecting group, which can be replaced by a hydrogen atom via ester hydrolysis or hydrogenation ether degradation, $R^9$ is an ester group which can be removed by base or acid hydrolysis, or by hydrogenation, and $R^{10}$ is an alcohol protecting group, which can be replaced by a hydrogen atom via ester hydrolysis or hydrogenation ether degradation, and wherein $R^{10}$ is selectively removable with respect to the $R^6$ alcohol protecting group; and (d) selectively removing the $R^6$ alcohol protecting group and $R^9$ ester group of the compound of formula (V) produced in (c), and cyclizing the 3 position alcohol group with the 1 position acid group using a lactone cyclizing catalyst, such as benzene-sulphonyl chloride, in a solvent such as pyridine at a temperature of about −10 to 10° C., and optionally replacing the $R^{10}$ alcohol protecting group of formula (V) with a hydrogen atom, to yield a (3S, 4S, 6S) oxetanone compound of the formula (I):

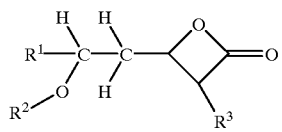

or a salt thereof.

In a preferred aspect, the process provides a compound of formula (I) wherein R1 is undecyl, $R^3$ is hexyl and $R^2$ is hydrogen, which is (2S, 3S, 5S) tetrahydroesterastin.

In another aspect the present invention relates to coupling such compound of formula (I) to an acyl compound via an acid or base esterification procedure without inversion of the 5S hydroxy group.

In another aspect the present invention provides a novel intermediate (2S, 3S, 5S) compound of the formula:

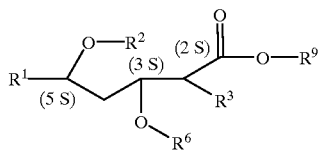

wherein:

$R^1$ and $R^3$ are each independently a $C_1$ to $C_{18}$ straight or branched alkyl hydrocarbon chain, and $R^2$ is hydrogen or an alcohol protecting group $R^{10}$, wherein $R^{10}$ can be replaced by a hydrogen atom via ester hydrolysis or hydrogenation ether degradation, and $R^{10}$ is selectively removable with respect to the $R^6$ alcohol protecting group, $R^6$ is an alcohol protecting group, which can be replaced by a hydrogen atom via ester hydrolysis or hydrogenation ether degradation, and $R^9$ is an ester group which can be removed by base or acid hydrolysis, or by hydrogenation, or, a salt thereof.

In a preferred aspect, the invention providessuch an intermediate compound wherein $R^1$ is undecyl or heptadecyl and $R^3$ is ethyl or hexyl, or a salt thereof.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain. branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure "and " $C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —CH$_2$—.

Preferred Embodiments

In one embodiment the present invention relates to novel process for making in at least 70% enantiomeric purity a (3S, 4S, 6S) oxetanone compound of the formula (I),:

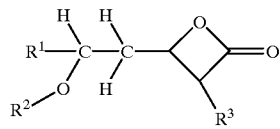

or a salt thereof
wherein:
 $R^1$ and $R^3$ are each independently a $C_1$ to $C_{18}$ straight or branched alkyl hydrocarbon chain, and
 $R^2$ is hydrogen or an alcohol protecting group $R^{10}$, wherein $R^{10}$ can be replaced by a hydrogen atom via ester hydrolysis or hydrogenation ether degradation. comprising the steps of:
  (a) selectively hydrogenating a composition comprising a compound which is a member selected from the group consisting of (6R) tetrahydro-2H-pyran-2-one compound of formula (II) and (6R) 5,6-dihydro-2H-pyran-2,4-dione of formula (IIa):

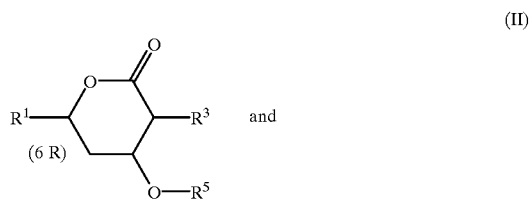

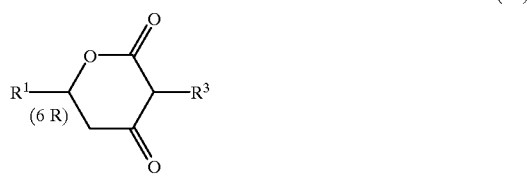

wherein
 $R^5$ is hydrogen or an alcohol protecting group, which can be replaced by a hydrogen atom via hydrogenation, and $R^1$ and $R^3$ are defined as in formula (I), by hydrogenating the compound of formula II with a hydrogenation catalyst selected from the group consisting of PtO$_2$, Raney Nichel and the like, and exchanging hydrogen atoms at the 3 and 4 ring positions or oxidizing the 4-oxo group to provide a (3S, 4S, 6R) 4-hydroxy-tetrahydro-2H-pyran-2-one compound of the formula (III):

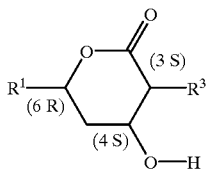

wherein $R^1$ and $R^3$ are defined as in formula (I);
(b) re-protecting the 4-hydroxy group of the compound of formula (II) produced in (a) with an ether protecting group $R^6$, which can be replaced by a hydrogen atom via ester hydrolysis or hydrogenation ether degradation, opening the lactone ring and esterifying the resulting free acid group to provide a (2S, 3S, 5R) [$R^7$] 2-[$R^3$]-3-[$R^{6-}$-oxy]-5-[hydroxy, $R^1$ pentanoic acid ester compound of the formula (IV):

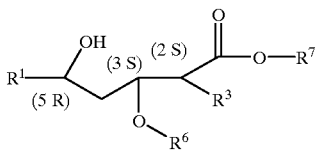

wherein
$R^1$ and $R^3$ are defined as in formula (I),
$R^6$ is an alcohol protecting group, which can be replaced by a hydrogen atom via ester hydrolysis or hydrogenation ether degradation, and
$R^7$ is an ester group which can be removed by base or acid hydrolysis, or by hydrogenation;
(c) inverting the chirality of the 5-hydroxy group of the compound of formula (IV) produced in step (b), wherein the inversion comprises a step which is a member selected from the group consisting of
(i) a Mitsunobu reaction,
(ii) esterifying the 5-hydroxy group to a carboxylic acid ester such as the trichloroacetic acid ester, and the like, and hydrolyzing the resultant ester in a water ether solvent such as 3:1 $H_2O$/dioxane, and
(iii) esterifying the 5-hydroxy group to a sulfonic acid ester, such as p-toluene sulfonic acid ester and the like, and reacting the ester with an excess of an organic acid salt selected from the group consising of potassium acetate, sodium acetate. tetraethylammonium acetate, and the like, to provide an ester exchange with the organic acid, wherein the free inverted (5S) 5-hydroxy group of (i) and (ii) is esterified with a hydroxy protecting group $R^{10}$ which can be which can be replaced by a hydrogen atom via ester hydrolysis or hydrogenation ether degradation, to provide a compound of the formula (V):

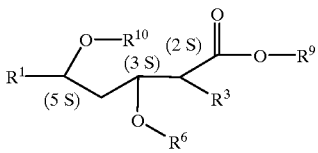

wherein
$R^1$ and $R^3$ are defined as in formula (I),
$R^6$ is an alcohol protecting group, which can be replaced by a hydrogen atom via ester hydrolysis or hydrogenation ether degradation, $R^9$ is an ester group which can be removed by base or acid hydrolysis, or by hydrogenation, and
$R^{10}$ is an alcohol protecting group, which can be replaced by a hydrogen atom via ester hydrolysis or hydrogenation ether degradation, and wherein $R^{10}$ is selectively removable with respect to the $R^6$ alcohol protecting group; and
(d) selectively removing the $R^6$ alcohol protecting group and $R^9$ ester group of the compound of formula (V) produced in (c), and cyclizing the 3 position alcohol group with the 1 position acid group using a lactone cyclizing catalyst, such as benzenesulphonyl chloride, in a solvent such as pyridine at a temperature of about −10 to 10° C., and optionally replacing the $R^{10}$ alcohol protecting group of formula (V) with a hydrogen atom, to yield a (3S, 4S, 6S) oxetanone compound of the formula (I):

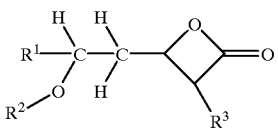

or a salt thereof
In a preferred aspect, the process provides a compound of formula (I) wherein R1 is undecyl, $R^3$ is hexyl and $R^2$ is hydrogen, which is (2S, 3S, 5S) tetrahydroesterastin.
In another aspect the present invention relates to coupling such compound of formula (I) to an acyl compound via an acid or base esterification procedure without inversion of the 5S hydroxy group.
In another aspect the present invention provides a novel intermediate (2S, 3S, 5S) compound of the formula:

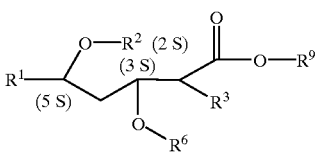

wherein:
$R^1$ and $R^3$ are each independently a $C_1$ to $C_{18}$ straight or branched alkyl hydrocarbon chain, and
$R^2$ is hydrogen or an alcohol protecting group $R^{10}$, wherein $R^{10}$ can be replaced by a hydrogen atom via ester hydrolysis or hydrogenation ether degradation, and $R^{10}$ is selectively removable with respect to the $R^6$ alcohol protecting group,
$R^6$ is an alcohol protecting group, which can be replaced by a hydrogen atom via ester hydrolysis or hydrogenation ether degradation, and
$R^9$ is an ester group which can be removed by base or acid hydrolysis, or by hydrogenation,
or, a salt thereof.
In a preferred aspect, the invention provide such intermediate compounds wherein $R^1$ is undecyl or heptadecyl and $R^3$ is ethyl or hexyl, or a salt thereof.
In a preferred aspect, the above process comprises making a (3S, 4S, 6S) oxetanone compound of the formula (I), or a salt thereof, in at least 90% enantiomeric purity:
In another preferred aspect the present invention provides a process for making a compound wherein $R^1$ is undecyl or heptadecyl and $R^3$ is ethyl or hexyl in at least 90% enantiomeric purity:

In one aspect the invention provides a process wherein the compound of formula (II) in step (a) is present at a ratio of from 90 to 100% with respect to the corresponding (6S) enantiomer, and comprises the step of isolating such a compound of formula (II) in an enantiomeric excess of from 90 to 100% with respect to the corresponding (6S) enantiomer.

In a preferred aspect the invention provides a process wherein the compound of formula (II) in step (a) is present at a ratio of greater than 97% with respect to the corresponding (6S) enantiomer, and comprises the step of isolating such a compound of formula (II) in an enantiomeric excess of greater than 97% with respect to the corresponding (6S) enantiomer.

The present invention provides a process as described above, which further comprises isolating a compound which is a member selected from the group consisting of the 6R compound of formula (IV), or its corresponding (6R, 3RS, 4RS) racemate with an alcohol protected 3 hydroxyl group, from a compound which is a member selected from the 6S, 3R, 4R enantiomer with an alcohol protected 3 hydroxyl group corresponding to the compound in formula (IV) and a compound which is the (6S, 3RS, 4RS) racemate corresponding to the compound of formula (IV), comprising a separation step with is a member selected from the group consisting of:
(i) selectively esterifying the 6-position hydroxyl group in the presence of a lipase such as PS 30, porcine pancreas lipase, and the like, and separating the ester from the alcohol,
(ii) selectively hydrolyzing an ester an ester of the 6-position hydroxyl group via a lipase such as PS 30, porcine pancreas lipase, and the like, and separating the ester from the alcohol,
(iii) forming a chiral salt with a chiral alcohol resolving agent such as L-alaninol, D-alaninol, L-tartaric acid, D-tartaric acid, S-methylbenzyl-amine, D-methylbenzylamine in an appropriate solvent such as methyl acetate, and the like, and separating the two enantiomers by re-crystallization; and
(iv) other known chiral alcohol separating procedures, and removing any ester or protecting groups from the 6R chiral hydroxyl group.

In another preferred aspect, the present invention provides such a process which further comprises the steps of
(a) inverting the 5S hydroxyl group of a (2R, 3R, 5S or 2RS, 3RS, 5S) [$R^7$] 2-[$R^3$]-3-[$R^6$—oxy]-5-[hydroxy, $R^1$] pentanoic acid ester compound of the formula (VII):

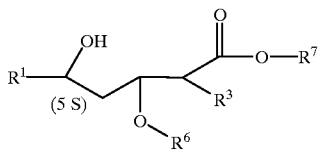

wherein
$R^1$, $R^3$, $R^6$ and $R^7$ are defined as in formula IV; wherein the inversion comprises a step which is a member selected from the group consisting of
(i) a Mitsunobu reaction, and freeing the hydroxyl group
(ii) esterifying the 5-hydroxy group to a carboxylic acid ester such as the trichloroacetic acid ester, and the like, and hydrolyzing the resultant ester in a water ether solvent such as 3:1 $H_2O$/dioxane to the inverted hydroxyl group, (iii) esterifying the 5-hydroxy group to a sulfonic acid ester, such as p-toluene sulfonic acid ester and the like, and reacting the ester with an excess of an organic acid salt selected from the group consising of potassium acetate, sodium acetate, tetraethylammonium acetate, and the like, to provide an ester exchange with the organic acid, and hydrolyzing the organic acid ester to the inverted hydroxyl group,
(iv) other known chiral alcohol inversion procedures,
(b) hydrolyzing the $R^7$ ester group to provide the free acid compound of the formula (VIII):

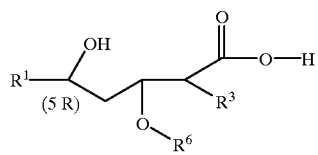

wherein
$R^1$, $R^3$ and $R^6$ and $R^7$ are defined as in formula (VII), and
(c) cyclizing the inverted alcohol group of the compound of formula (VIII) with the 1 position acid group in the presence of a lactone cyclizing catalyst such as tonuene-4-sulfonic acid monohydrate in an alcohol at about 50–60° C. to provide a 6R tetrahydro-2H-pyran-2-one compound of formula (IX):

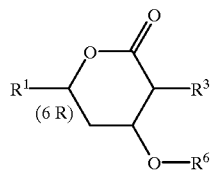

wherein
$R^1$, $R^3$, $R^6$ and $R^7$ are defined as in formula (VIII); and
(d) selectively hydrogenating the (6R) tetrahydro-2H-pyran-2-one compound of formula (IX) with a hydrogenation catalyst selected from the group consisting Of $PtO_2$, Raney Nichel and the like, and exchanging hydrogen atoms at the 3 and 4 ring positions to provide a (3S, 4S, 6R) 4-hydroxy-tetrahydro-2H-pyran-2-one compound of the formula (IV):

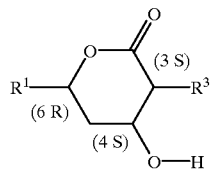

wherein $R^1$ and $R^3$ are defined as in formula (I).

The intermediate compounds of formulae (II) and (IV) can be efficiently made from commercially feasible materials by adapting several methods known in the art and by refining the synthesis to avoid unnecessary or costly steps. Further, the following non-limiting reaction schemes, some steps of which are novel, are merely to exemplify the invention.

A process for making an intermediate compound for synthesizing a compound of the formula:

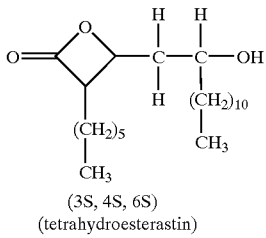

(3S, 4S, 6S)
(tetrahydroesterastin)

comprising the steps of:

treating dodecyl aldehyde (lauraldehyde) with a saturated aqueous solution of a bisufite such as sodium bisulfite to form a bisulfite salt of the formula:

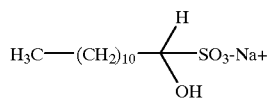

(b) reacting the bisulfite salt with a 2-haloacetic acid R ester, such as 2 bromoacetic acid ethyl ester in a suitable solvent such as THF and water and in the presence of a catalytic amount of an acid such as HCl to produce a ketone derivative of the formula:

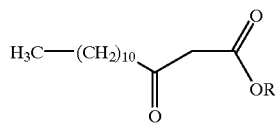

(c) reducing the ketone derivative with $NaBH_4$, or the like, and optionally resolving the R and S enantiomer by forming an ester under chiral resolving conditions, such as esterifying the alcohol in the presence of the pseudomonas lipase PS 30 and the like, or by reducing the ketone carbonyl group with a chiral hydrogenation catalyst, at a temperature from 0° C. to 50° C., preferably at room temperature, in a suitable solvent, such as ethanol and the like, or reducing the ketone group with a chiral borane such as DIP-Cl (Aldrich) and protecting the alcohol with a protecting group (P1), such as t-butylidimethylsilyl by reaction with t-butyldimethylchlorosilane in dimethylformamide (DMF), to provide a compound of the formula:

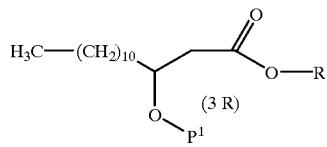

(d) reacting the protected alcohol with at least one equivalent of a base such as NaOH followed by at least 1 equivalent of HCl to provide the free acid compound, and reacting the mono free acid with an acid reducing agent such as BF3—THF to produce the corresponding aldehyde of the formula:

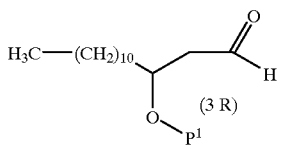

(e) reacting the aldehyde with a 2-halogenoctanoate (such as ethyl 2-bromooctanoate) to produce a ketone compound of the formula:

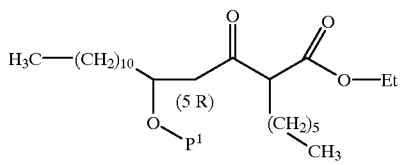

(f) reducing the 3 ketone derivative with NaBH4, or the like, then removing the $P^1$ protecting group from the 5 hydroxy in a solvent such as an alcohol, e.g., ethanol in the presence of an acid catalyst such as pyridinium-4-toluenesulphoneate or tetrabutylammonium fluoride trihydrate in THF while heating at about 50–65° C., followed by hydrogenating the ester group with hydrogen and Pd/C to yield the free acid diol as follows:

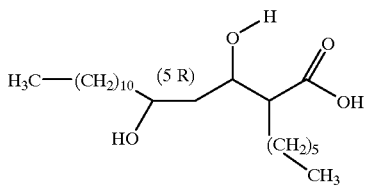

(g) and then cyclizing the 5R alcohol with the free acid to provide a 6R pyranolone ring by heating the free acid compound at a temperature from 50° C. to 60° C. in ethanol in the presence of toluene-4-sulfonic acid to provide a compound of the formula:

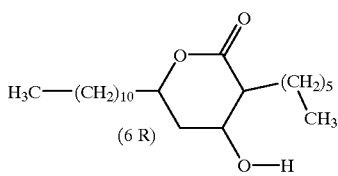

which may be utilized as the formula (II) compound described above.

Alternatively, the chiral ketone reducing agent utilized to reduce the beta oxo dodecanoic acid can be omitted to obtain a racemate. The racemate can be utilized as the formula (II) compound, followed by resolving the resulting (2S, 3S, 5R) formula (IV) enantiomer from its (2R, 3R, 5S) formula (VII) enantiomer.

Another process for making an intermediate compound for synthesizing a compound of the formula:

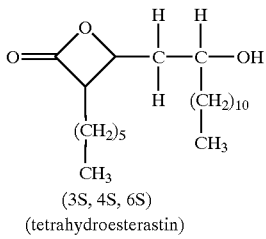

(3S, 4S, 6S)
(tetrahydroesterastin)

comprises the steps of:

(a) treating dodecyl halide (lauric acid chloride) with a N,O-dimethylhydroxyl- amine hydrochloride in a 1:1.5 ratio in acetonitrile, triethylamine and 1-(3-dimethylaminopropyl)-3-ethylcarbodiimide hydrochloride and stirring at room temperature for about 5 hours to provide a compound of the formula:

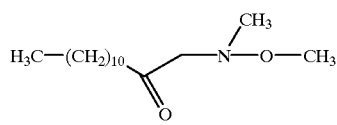

(b) reacting the N-methoxymethyl amide carboxylic acid derivative with an organometallic salt of an acetic acid R ester (or a salt of a two halo acetic acid R ester), such as 2-lithium acetic acid ethyl ester in a suitable solvent such as dry THF under nitrogen or argon and the reaction is quenched with an acid such as HCl to produce a ketone derivative of the formula:

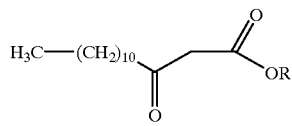

(c) forming the tetradecyl acyl halide (for example the acid chloride) of the ketone compound and reacting it with a N,O-dimethylhydroxyl- amine hydrochloride in a 1:1.5 ratio in acetonitrile, triethylamine and 1-(3-dimethylaminopropyl)-3-ethylcarbodiimide hydrochloride and stirring at room temperature for about 5 hours to provide a compound of the formula:

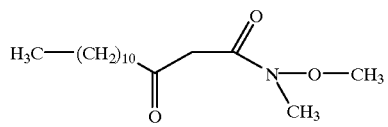

(d) reacting the N-methoxymethyl amide carboxylic acid derivative with an alpha organometallic salt of an lower alkyl acid R ester (or a salt of an alpha halo lower alkyl acid R ester), such as 2-lithium octanoic acid ethyl ester in a suitable solvent such as dry THF under nitrogen or argon and quenching the reaction with an acid such as HCl, and the like to produce a 3,5 diketone derivative of the formula:

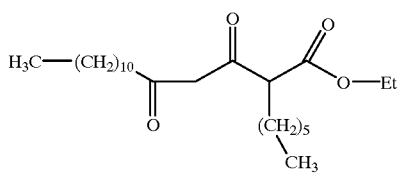

(e) reducing the 3,5 diketone acid derivative with $NaBH_4$, or the like, to yield the free acid diol as follows:

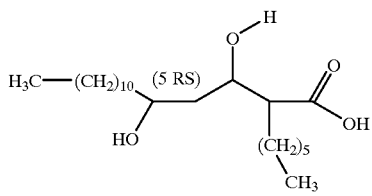

and (f) cyclizing the 5RS alcohol with the free acid to provide a 6R pyranolone ring by heating the free acid compound at a temperature from 50° C. to 60° C. in ethanol in the presence of toluene-4-sulfonic acid to provide a compound of the formula:

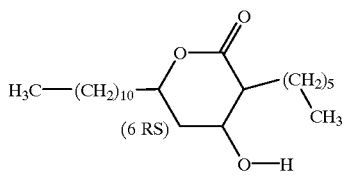

which may be utilized as the formula (II) compound described above.

Alternatively, the diketone reduction step of step (e) can be conducted with a chiral borane reducing to obtain a (2RS, 3R, 5R) which when cyclized provides the (3RS, 4R, 6R) compound, which can be utilized as the formula (II) compound.

A further process for making an intermediate compound for synthesizing a compound

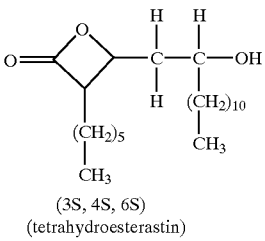

(3S, 4S, 6S)
(tetrahydroesterastin)

comprises the steps of:

(a) reaction methyl 2-acetyloctanate (Aldrich 10887) with a organometallic base, such as butyllithium salt to deprotonate the tertiary carbon atom of the 2-acetyl group, (b) reacting the lithium organometallic salt in a suitable solvent such as THF with a lauric acid halide (dodecoyl chloride) of the formula:

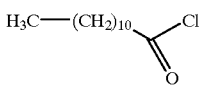

to provide a 3,5 diketone compound of the formula:

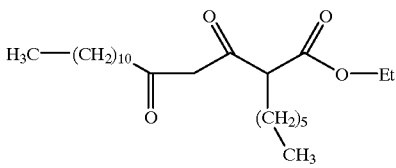

(c) reducing the 3,5 diketone acid derivative with NaBH$_4$, or the like, to yield the free acid diol as follows:

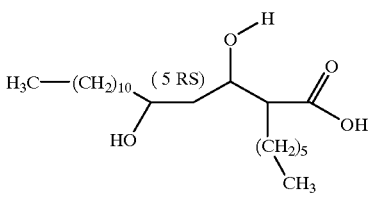

and (d) cyclizing the 5RS alcohol with the free acid to provide a 6R pyranolone ring by heating the free acid compound at a temperature from 50° C. to 60° C. in ethanol in the presence of toluene-4-sulfonic acid to provide a compound of the formula:

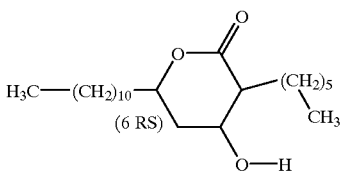

which may be utilized as the formula (II) compound described above.

Alternatively, the diketone reduction step of step (c) can be conducted with a chiral borane reducing agent to obtain a (2RS, 3R, 5R) which when cyclized provides the (3RS, 4R, 6R) compound, which can be utilized as the formula (II) compound.

In one aspect of the present invention, there is provided a chiral alcohol resolution process step which incorporates a lipase to hydrolyze esters of the intermediate alcohols, or to be present during an esterification step, wherein the lipase may be a lipase such as the pseudomonas PS 30, pig pancreas lipase, and the like.

The (2S, 3S, 5S) oxetanone compounds provided by the processes according to the invention may be linked to other compounds or a support by esterifying with an acyl, acyl halide, or by a transesterification process. In a preferred embodiment the lipase inhibitiors according to the invention are linked via a terminal ether/terminal ester bridge, to a oil or lipid absorbable polymer moiety. Preferably, the free 5-hydroxyl (2S, 3S, 5S) compounds are linked under acidic conditions to a polysaccharide such as chitosan, which polysaccharide has been modified to have an acyl, or acyl halide attachment group.

Non-limiting examples of preferred bridges between the lipase inhibitor oxetanone moiety produced according to the present invention and the polymer moiety includes at least one ether bridge formed from an alcohol group on the polymer moiety and at least one ester or carboxamide bond between the 5-hydroxy group of the oxetanone. Further preferred is a process for producing a compound wherein at least one amino acid derivative is located in the bridge, and is bound directly or indirectly to the 5 hydroxyl position on the 1,3 oxetanone moiety via an ester linkage.

The preferred compounds produced from such linkage with a polysaccharide also includes their pharmaceutically acceptable isomers, hydrates, solvates, salts and prodrug derivatives.

A preferred aspect of the present invention relates to a process for making novel oxetanone derivatives of the formula Ia, as follows:

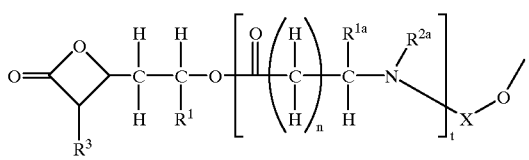

wherein:
  t is an integer from 0 to 1
  X—O—Q is an ether linkage wherein:
    X of the ether linkage is a bridging group, and
    Q of the ether linkage is a polysaccharide of a sufficient molecular weight or property that such polysaccharide is not absorbed by the digestive system of a mammal such as a dog, cat, non-human primate or a human primate, which polysaccharide is further defined below;
  $R^1$ and $R^3$ is defined as in formula (I) of the (2S, 3S, 5S) 5-hydroxyl oxetanone compounds, produced by a process according to the invention as described above,;
  $R^{1a}$ is a member selected from the group consisting of:
    Hydrogen,
    Ar,
    Ar—$C_{1-5}$-alkyl and
    $C_{1-10}$-alkyl interrupted by 0–3 members independently selected from the group consisting of an oxygen atom, a sulfur atom, a sulfinyl group, a sulfonyl group, a —N(—$R^{4a}$ group, a —C(=O)—N(—$R^{4a}$ group, and a —N(—$R^{4a}$)—C(=O)— group, wherein 0–3 carbon atoms of the $C_{1-10}$-alkyl group can be substituted independently by a member selected from the group consisting of a hydroxy group, thiol group, $C_{1-10}$-alkoxy group, a $C_{1-10}$-alkylthio group, a —N(—$R^{5a}$,—$R^{6a}$) group, a —C(=O)—N($R^{7a}$, —$R^{8a}$) group, and a —N(—$R^{9a}$)—C(=O)—$R^{10a}$ group;
  $R^{2a}$ is a member selected from the group consisting of:
    hydrogen and $C_{1-6}$-alkyl, or $R^{2a}$ taken with $R^{1a}$ forms a 4–6 membered saturated ring containing 0–4 nitrogen atoms wherein the ring may be substituted by 0–4 $R^{11}$ groups:
  $R^{4a}$-$R^{10a}$ are each independently a member selected from the group consisting of:
    hydrogen and $C_{1-6}$-alkyl;
  n is an integer of 0–3;
and all pharmaceutically acceptable isomers, salts, hydrates, solvates and prodrug derivatives thereof.

A preferred compound according to formula Ia is a compound wherein X is a member selected from the group consisting of:

—(C(=O))$_{0-1}$—X$_a$—, wherein X$_a$ is a member selected from the group consisting of:

a straight or branched chained divalent $C_{1-17}$-alkylene group which is saturated or optionally interrupted by up to eight double or triple bonds;

a straight or branched chained divalent $C_{1-17}$-alkylene group which is saturated or optionally interrupted by one or more members selected from the group consisting of:
an oxygen atom,
a sulfur atom,
a sulfonyl group,
a sulfinyl group,
a substituted or unsubstituted 6–10 member monocyclic or bicyclic aryl or heteroaryl group having from 1–4 ring hetero atoms selected from the group consisting of O, N, S,
a —NH— group, wherein the hydrogen atom may be replaced with a $C_{1-10}$ alkyl group
a —C(=O)— group,
a —NH—C(=O)— group, wherein the hydrogen atom may be replaced with a $C_{1-10}$ alkyl group and
a —C(=O)—NH— group, wherein the hydrogen atom may be replaced with a $C_{1-10}$ alkyl group a straight or branched chained divalent $C_{1-17}$-alkylene group which is saturated or optionally interrupted by up to eight double or triple bonds and is interrupted in a position other than alpha to an unsaturated carbon atom by one or more members selected from the group consisting optionally interrupted by one or more members selected from the group consisting of:
an oxygen atom,
a sulfur atom,
a sulfonyl group,
a sulfinyl group,
a substituted or unsubstituted 6–10 member monocyclic or bicyclic aryl or heteroaryl group having from 1–4 ring hetero atoms selected from the group consisting of O, N, S,
a —NH— group, wherein the hydrogen atom may be replaced with a $C_{1-10}$ alkyl group
a —C(=O)— group,
a —NH—C(=O)— group, wherein the hydrogen atom may be replaced with a $C_{1-10}$ alkyl group and
a —C(=O)—NH— group, wherein the hydrogen atom may be replaced with a $C_{1-10}$ alkyl group divalent phenylene or divalent naphthylene substituted on the ring structure by 0–4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and -$C_{1-6}$-alkyl-SH;

divalent biphenylene substituted by 0–6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

phenoxyphenylene substituted by 0–6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

divalent phenylthiophenylene substituted by 0–6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and and all pharmaceutically acceptable isomers, salts, hydrates, solvates and prodrug derivatives thereof.

More preferred is compound according to formula Ia, wherein X is a member selected from the group consisting of:

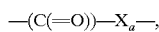

and $X_a$ is a member selected from the group consisting of:

a straight or branched chained divalent $C_{1-17}$-alkylene group which is saturated or optionally interrupted by up to eight double or triple bonds.

Further preferred are compounds according to formula Ia, wherein $R^1$ is undecyl, $R^3$ is hexyl, $R^{1a}$ is straight or branched chain $C_1$–$C_8$ alkyl, $R^{2a}$ is hydrogen and X is a member selected from the group consisting of:

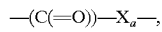

and Xa is a member selected from the group consisting of divalent saturated $C_5$–$C_{18}$ alkylene, and more preferably, Xa is a divalent saturated pentylene or undecylene group, or a salt thereof.

Preparation of Compounds

The lipase inhibitor compounds, polymer moieties and bridging groups of the present invention may be synthesized or readily obtained from commercially available sources. Preferably, the (2S, 3S, 5S) 5-hydroxyl oxetanone lipase inhibitor compounds are obtained by a process as described above. Polymer bridging groups, bridge coupling processes and compound purification methods are described and referenced in standard textbooks, particularly the coupling of alcohol groups via diether bridges, ether/ester bridges, ether/ketone bridges and the like. Standard polymer textbooks reference typical bifunctional bridging groups and coupling procedures.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups may be protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference. Alcohol and ester protecting group may also be utilized.

Lipase inhibitor moieties having a free hydroxy group such as the oxetanones described above, and the like, are easily coupled to a polymer moiety having free hydroxy groups such as cellulose, chitosan and other polysaccharides having free hydroxyl groups. One or both of the lipase inhibitor moiety and the polymer moiety may be derivitized to form part of the linking bridge prior to reacting with the other moiety. For example, a desired number of the hydroxy groups of the polysaccharides, such as chitosan, may be functionalized with a compound having a terminal acyl or ester group such as 6-bromohexanoic acid, 12-bromododecanoic acid, and the like, or an ester derivative of such acids, and subsequently the 5-hydroxyl group of the oxetanone lipase inhibitor molecule may be condensed with the ester group or a terminal acyl group (the acyl group may be modified with an halide group to an acyl halide group, such as the acyl chloride) to form an ester linkage with the ether bridged polymer moiety as shown in polysaccharide chemistry. In one procedure a polymer moiety such as chitosan can be reacted with a compound such as a halomethylbenzoic acid ester, loweralkyl 6-bromohexanoic acid, lower alkyl 12-bromododecanoic acid, or the like, and de-esterified to present a free acid group which may be, activated further by forming the acyl halider, and reacted with a terminal portion of the lipase inhibitor (which may have been esterified with a bridging compound which has a functional group capable of reacting with an ester or acyl group) to form an ester, ketone, or carboxamide with the optionally derivitized lipase inhibitor moiety.

In one preferred aspect of the invention, one of the two moieties is reacted with an asymmetrical halide/acyl bridging group, such as a terminal halide alkanoic acid of 1:1 to etherize a free hydroxyl group, replace a hydrogen atom on an amino group, or foom a ketone with an acid group, and the resulting intermediate can then be reacted with the an alcohol or amino moiety to form an ester group or a carboxamide group with a free alcohol group, or by replacing a nitrogen atom on a amino group. Particularly preferred polymer moieties are polysaccharides having multiple free hydroxyl group which after coupling may optionally be sulfonated to render the lipase moiety itself a lipase inhibitor compound. Etherification, amination and ketone formation procedures are well-known in the art and well within the routine skill of the ordinary practitioner. Further, other bridging groups and the techniques for binding a compound having a reactive functional group to a polymer moiety are well-known in the art. The preferred compounds also include their pharmaceutically acceptable isomers, hydrates, solvates, salts and prodrug derivatives.

The bridging group refers to a bifunctional chain or spacer group capable of reacting with one or more functional groups on a lipase inhibitor compound and then react with a second same or different functional group on a polymer compound in order to form a linked structure or conjugate between the two compounds. The bond formed between the bridging group and each of the two compounds is preferably of a type that is resistant to cleavage by the digestive environment, other than to inhibit a lipase by binding substantially irreversibly.

By appropriate selection of the type of bridging group reactant, different structural groups with various chemical properties can be incorporated into the resulting bridge and various types of lipase inhibitors can be connected to a nonabsorbable polymer moiety, such as a polysaccharide, and preferably to chitosan. Reaction temperatures and other reactions conditions, as well are reactant proportions are well within the skill of the ordinary polymer chemist practitioner. Other groups and modifications will be apparent to one of ordinary skill in the art from the above discussion.

The lipase inhibitor functionality of the coupled lipase inhibitors may be determined by well-known lipase inhibitor assays. A therapeutically effective amount of the bound lipase inhibitor may be administered to a patient. Additional fat binding polymers may optionally be added to the composition.

The following non-limiting reaction Schemes I, II, III and IV illustrate preferred embodiments of the invention with respect to making compounds according to the invention.

Scheme I

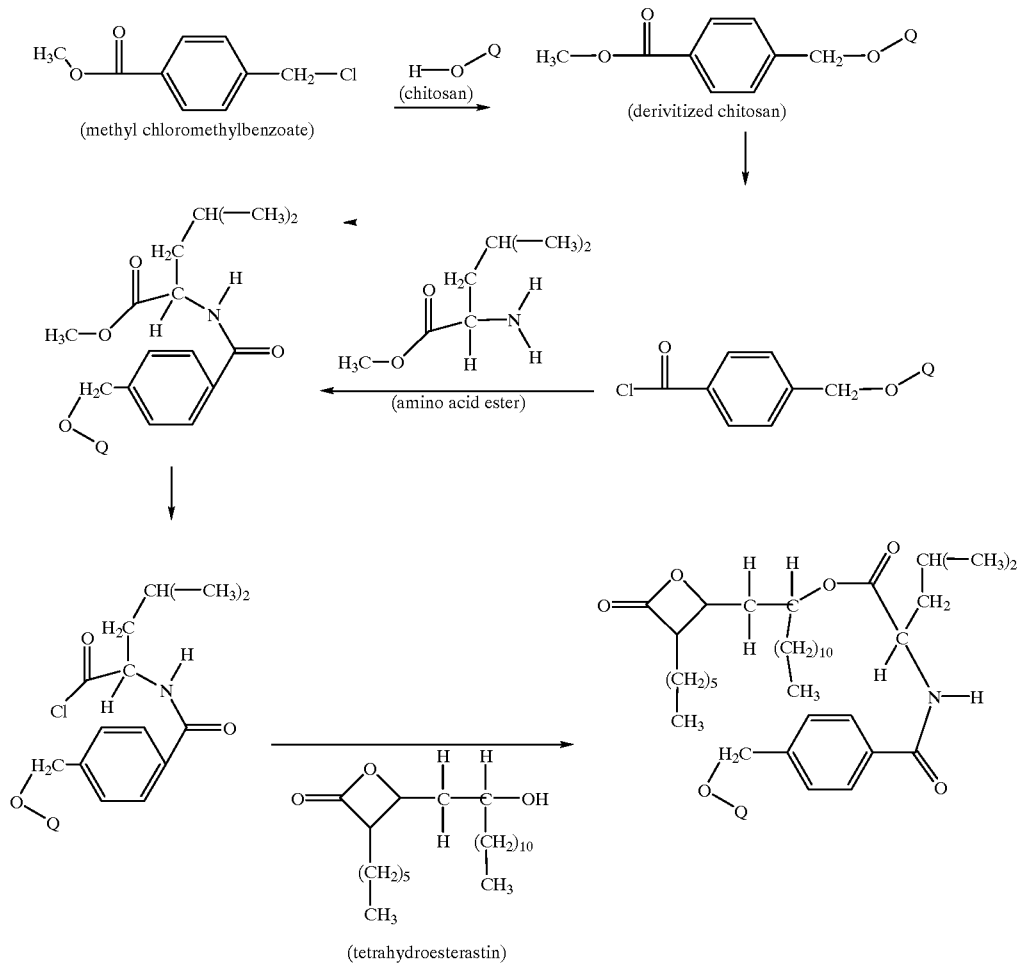

(tetrahydroesterastin)

Scheme II
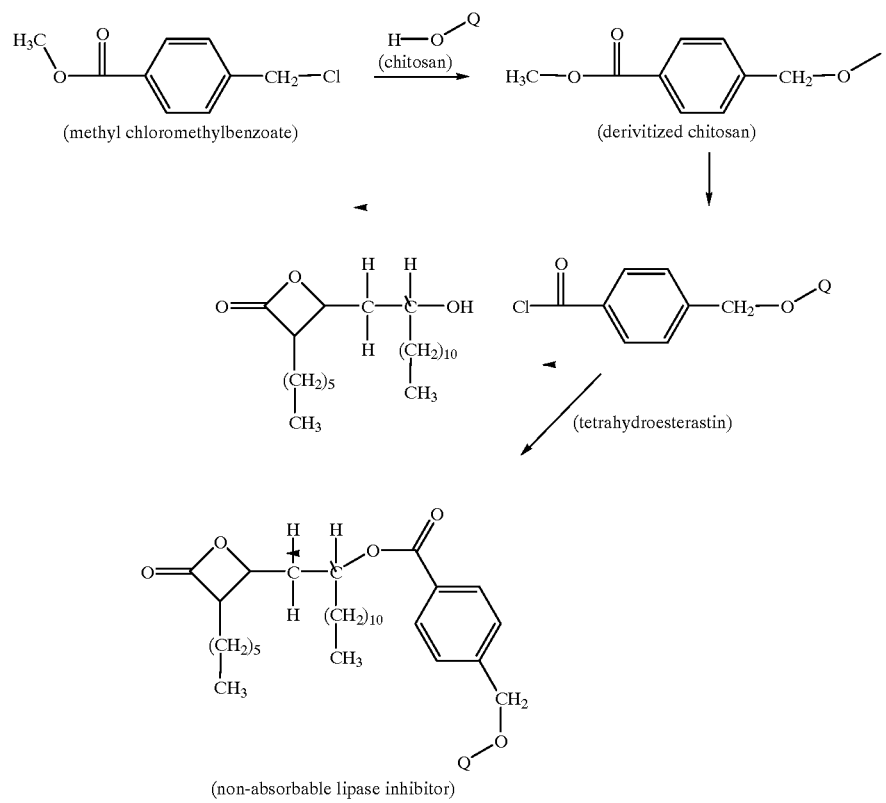
Scheme III
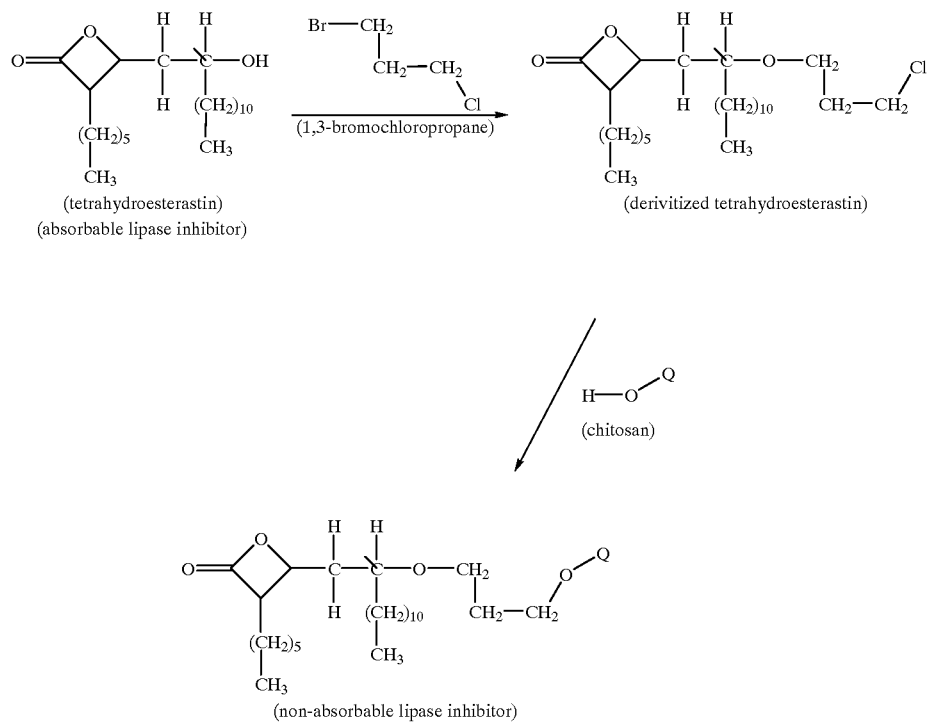

Scheme IV

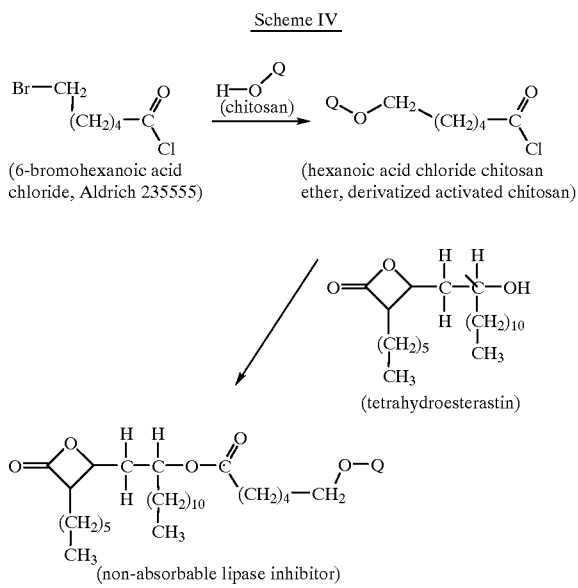

Scheme V

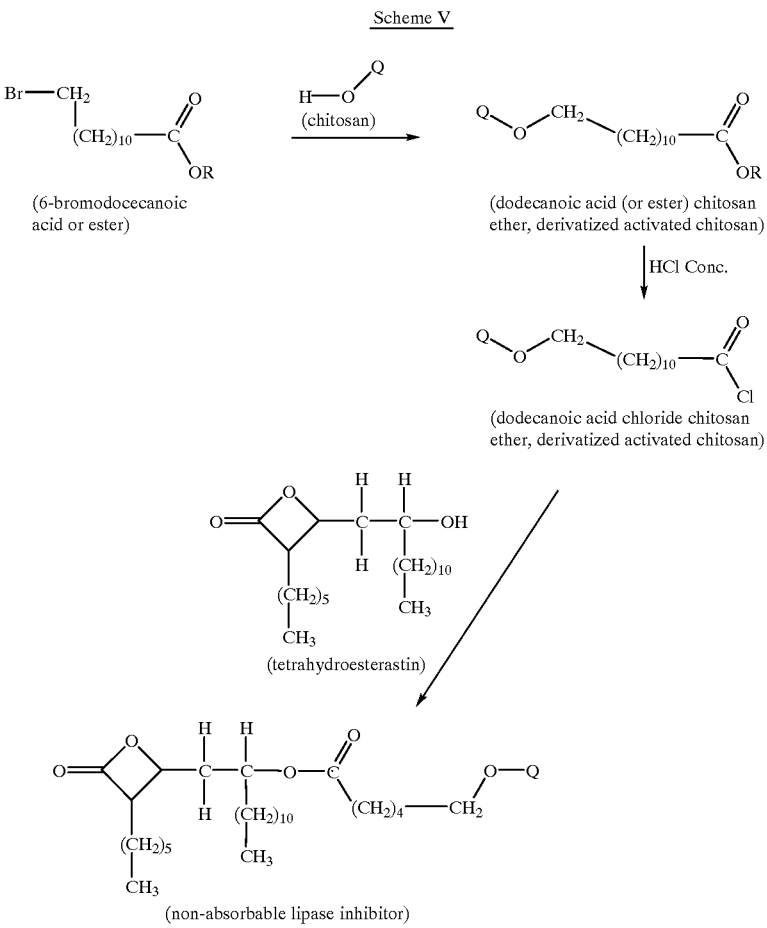

Such chitosan derivatives provide a lipase inhibitor with very low absorption rates, and at such rates tetrahydroesterastin is not known to be substantially toxic.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by oral tablets, capsules or other unit dose mechanisms, such as liquids, other methods of administration are also anticipated such as in food stuffs, employing a variety of dosage forms. The compounds of this invention are desirably incorporated into food articles which may include fats to prevent their absorption.

The compounds of this invention may also be coupled with suitable polymers to enhance their therapeutic effects. Such polymers can include lipophilic polymers, such as polysaccharides and the like.

Therapeutically effective dosages may be determined by either in vitro or in vivo methods. For each particular compound of the present invention, individual determinations may be made to determine the optimal dosage required.

The range of therapeutically effective dosages will naturally be influenced by the route of administration, the therapeutic objectives and the condition of the patient. For routes of administration, the lipase inhibitor activity, in view of the amount of fat consumed, must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

Typically, about 500 mg to 3 g of a lipase inhibitor compound or mixture of lipase inhibitor compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained. The addition, one or more other therapeutic ingredients such as a fat absorbing polysaccharide or fiber, a fat-specific lipase inhibitor or lipase, as well as other dietary agents may be utilized in therapeutically effective amounts.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as other weight control or lipase inhibitory products, cholesterol controlling drugs, and the like.

The compounds of this invention can be utilized in vivo, ordinarily in mammals such as non-human primates, humans, sheep, horses, cattle, pigs, dogs, cats, rats and mice, or in vitro.

The following non-limiting examples are provided to better illustrate the present invention.

EXAMPLE 1
Production of Mixed Hexyl 3-Oxo-tetradecanoate Esters

To a 20 L 3-neck flask equipped with a mechanical stirrer, argon inlet, reflux condenser, heating mantle and vacuum system, under argon is added a suspension 140 g of sodium hydride in 6 L of THF. The temperature is lowered to 0–5° C. and maintained as 1 Kg of mixed hexyl acetic acid esters (Aldrich 461253) are slowly added to this suspension with stirring. After one hour of stirring the mixture is cooled −10° C. and 1.25 Kg of 24% w/wn-Butyllithium (n-BuLi) (about 5 mol) in 3 L of hexane is added. After stirring at this temperature for 45 minutes, the flask is then cooled to below −5° C. followed by slowly adding 575 g of ethyl dodecanoate (Aldrich L4625). This solution is allowed to warm to −10° C. with stirring and is stirred at this temperature for 1 hour. The reaction solution is added under argon 1.25 L of 40% hydrochloric acid and 1.5 Kg of ice. The mixture is extracted twice with 5 L of hexane and water. The organic phases are combined, dried over magnesium sulfate, filtered, and the organic solvents are evaporated at reduced pressure to provide a solid residue (about 1.4 Kg).

Example 2
Production of (3R) 3-Hydroxy-tetradecanoic Acid

To a 20 L 3-neck flask equipped with a mechanical stirrer, argon inlet, reflux condenser, heating mantle, cooling apparatus, and vacuum system, under argon is added 8 mols (2.6 Kg) of (+)-β-chlorodiisopinocamphenylborane ("+-DIP-Cl"). To this was added 4 L of dry THF at room temperature over one hour. Once the mixture is dissolved together the temperature is lowered to −25° C. While maintaining the temperature between −20 and −25° C. the 1.4 Kg of mixed hexyl 3-oxo-tetradecanoate esters (Example 1) in 2 L of dry THF is slowly added with stirring (over a one hour period) to this solution. The reaction temperature is maintained between −10 and −20° C. for 8 hours and the reaction progress is monitored with HPLC. After the 8 hours, the temperature is allowed to gradually warm to about −5° C., and after 1 hour at this new temperature is allowed to warm to 0° C. in order to increase the rate of reaction. The reaction process is monitored by HPLC and the reaction is stopped after all the starting material is consumed. To the reaction mixture is slowly added 3 L of water (over a one hour period) while maintaining the reaction temperature below 10° C. About 4 L of methanol is then added, followed by 4 L of aqueous 5 M NaOH. The mixture is stirred at room temperature and the reaction is monitored by HPLC until it is complete (about two hours). The reaction mixture is allowed to separate and the aqueous layer is removed. The aqueous layer is extracted with hexane and the separated aqueous layer is neutralized with HCl, saturated with NaCl and extracted 3 times with 3×1 L of with warm hexane. The hexane layers are combined and concentrated by evaporation of the solvent at reduced pressure to provide a crude product which is dried over magnesium sulfate to provide about 1.3 Kg of solid.

EXAMPLE 3

Production of (3R)-3-Benzoyloxy-tetradecanoyl Chloride

To a 20 L 3-neck round bottom flask equipped with a mechanical stirrer, nitrogen inlet, reflux condenser, heating mantle, vacuum system, and scrubber system for efficient removal of HCl and $SO_2$ gases liberated during the reaction, is charged under nitrogen 15 moles of benzoic acid anhydride, 10 moles of concentrated anhydrous HCl in 4 L of THF, and 7.48 moles of the (3R)-3-hydroxy-tetradecanoic acid obtained from Example 1, above. The stirred mixture is placed under a $N_2$ flow, which is vented to the scrubber system. The stirred mixture is heated to reflux for 3 hours during which the reaction becomes complete. The resulting solution is neutralized with 1N NaOH and the organic layer is separated from the aqueous layer. The aqueous layer is washed with THF and the resulting organic portions are combined, placed under vacuum and THF is removed. The resulting solid is dissolved in warm hexane, cooled and worked up to provide the product (3R)-3-benzoyloxy-tetradecanoyl chloride in about 95% yield.

EXAMPLE 4
Production of 5R Ethyl 5-Benzoyloxy-2-hexyl-3-oxo-heexadecanoate Ester To a 20 L 3-neck flask equipped with a mechanical stirrer, argon inlet, reflux condenser, heating mantle and vacuum system, under argon is added a suspension 140 g of sodium hydride in 6 L of THF. The temperature is lowered to 0–5° C. and maintained as 1 Kg of ethyl octanoate (Aldrich 112321) is slowly added to this suspension with stirring. After one hour of stirring the mixture is cooled –10° C. and 1.25 Kg of 24% w/wn-Butyllithium (n-BuLi) (about 5 mol) in 3 L of hexane is added. After stirring at this temperature for 45 minutes, the flask is then cooled to below –15° C. followed by slowly adding 575 g of the (3R) 3-benzoyloxy-tetradecanoyl chloride from Example 3. This solution is allowed to warm to –10° C. with stirring and is stirred at this temperature for 1 hour. The reaction solution is added under argon 1.25 L of 40% hydrochloric acid and 1.5 Kg of ice. The mixture is extracted twice with 5 L of hexane and water. The organic phases are combined, dried over magnesium sulfate, filtered, and the organic solvents are evaporated at reduced pressure to provide a solid residue (about 1 Kg).

EXAMPLE 5
Production of 5R 3,5-Dihydroxy-2-hexyl-hexadecanoic Acid.

To a 20 L 3-neck flask equipped with a mechanical stirrer, argon inlet, reflux condenser, heating mantle and vacuum system, under argon 6 L of anhydrous THF is added and 1 Kg of 5R ethyl 5-benzoyloxy-2-hexyl-3-oxo-heexadecanoate ester is dissolved while gassing with argon, treated with 250 mL of MeOH and cooled to –5° C. Then 825 g of sodium borohydride is slowly added in portions with stirring in a manner that permits the temperature to not exceed 0° C. After stirring for 3 hours the excess sodium borohydride is filtered off, the reaction mixture is hydrolyzed (to about pH 6) with cold 2N hydrochloric acid at 0° C. The mixture is allowed to warm to room temperature and the solvent was evaporated off under vacuum. The residue is extracted twice with ether and the ether phases are combined and concentrated under vaccum. The crude concentrate is added to a solution of THF and aqeuous KOH and stirred at 35° C. for three hours. The organic phase is separated washed twice with cold water, dried over $MgSO_4$ and evaporated under reduced pressure. There is obtained about 1 Kg of 5R 3,5-dihydroxy-2-hexyl-hexadecanoic acid.

EXAMPLE 6
Production of (6R) 5,6-Dihydro-3-hexyl-4-hydroxy-6-undecyl-2H-pyran-2-one To a 20 L 3-neck flask equipped with a mechanical stirrer, argon inlet, reflux condenser, heating mantle and vacuum system, is charged under argon with 6 L of anhydrous toluene and the 1.3 Kg of product from Example 5 is slowly added to the solution with stirring pyridium para-toluenesulfonate and refluxed under argon for 2 hours to form the lactone. The reaction mixture is cooled to room temperature and washed twice with a saturated aqueous sodium carbonate solution. The organic phases are combined and evaporated under vacuum at about 40° C. to produce a product, and warm hexane is added to the product to dissolve it into a homogenous mixture. The warm hexane mixture is cooled to room temperature with stirring. The mixture is then cooled to –10° C. and stirred at that temperature for 15 hours. The crystalline solid is then filtered under suction. The filter cake is washed with cold hexane and dried over magnesium sulfate. The crystals are then dried overnight in a drier to remove any remaining solvent. About 1 Kg of (6R) 5,6-dihydro-3-hexyl-4-hydroxy-6-undecyl-2H-pyran-2-one, having a m.p. of 106–108° C. is provided.

EXAMPLE 7
Production of (3S, 4S, 6R) Tetrahydro-3-hexyl-4-hydroxy-6-undecyl-2H-pyran-2-one A hydrogenator is purged twice with nitrogen and charged with the 1 Kg of product from Example 6, which is dissolved in 6 L of anhydrous ethyl acetate, and 500 g of $PtO_2$ is added. The hydrogenator is purged twice with hydrogen and then charged with hydrogen at 50 bar. The temperature is raised to 40° C. and hydrogen flow is maintained at 50 bar for 12 hours. The catalyst is filtered off and the solution is evaporated. After dissolving in warm hexane, the product is cooled to 0° C. overnight and recrystallized to yield 900 g of (3S, 4S, 6R) tetrahydro-3-hexyl-4-hydroxy-6-undecyl-2H-pyran-2-one, having a m.p. of 108–109° C.

EXAMPLE 8
Production of (3S, 4S, 6R) Tetrahydro-3-hexyl-4-[(tetrahydro-2H-pyran-2-yl)oxy]-6-undecyl-2H-pyran-2-one The 900 g of (3S, 4S, 6R) tetrahydro-3-hexyl-4-hydroxy-6-undecyl-2H-pyran-2-one of Example 7, and 500 ml of freshly distilled 3,4-dihydro-2H-pyran are dissolved in 10 L of methylene chloride and cooled to about 3° C. and 9.6 g of p-toluenesulfonic acid monohydrate are added. The temperature rises to about 8° C. and the mixture is stirred at this temperature until the reaction is finished. The reaction mixture is washed with a mixture of 4 L of saturated aqueous sodium chloride solution, 4 L of saturated aqueous sodium hydrogen carbonate solution and 8 L of water. After drying the mixture over $MgSO_4$ the mixture is filtered and the solvent is removed. The resulting residue is utilized in the next step without further purification of the (3S, 4S, 6R) tetrahydro-3-hexyl-4-tetrahydro-2H-pyran-2-yl)oxy]-6-undecyl-2H-2-one.

EXAMPLE 9
Production of benzyl (2S, 3S, 5R) 2-Hexyl-5-hydroxy-3-[(tetrahydro-2H-pyran-2-yl)oxy]-hexadecanoic Acid Ester The product of Example 8 is dissolved in 6 L of THF under argon and anhydrous conc. sulphuric acid is added which is warmed to 30° C. and stirred for two hours. A metallic salt of benzyl alcohol (sodium salt) in an aqueous solution is slowly added in a 1:1.2 molar excess with respect to the hexadecanoic acid ester. The mixture is stirred for 4 hours at 25° C., the pH is then adjusted to 9 with NaOH, and the aqueous layer and organic layer are separated. The organic layer is extracted twice with 4 L of cold $H_2O$, and the organic layer is dried over magnesium sulfate. The resulting benzyl (2S, 3S, 5R) 2-hexyl-5-hydroxy-3-[(tetrahydro-2H-pryan-2-yl)oxy] hexadecanoic acid ester is used in the next step without purification.

EXAMPLE 10
Production of Benzyl (2S, 3S, 5S) 5-Benzoyloxy-2-hexyl-3-[(tetrahydro-2H-pyran-2-yl)oxy]-hexadecanoic Acid Ester The product of Example 9, triphenylphosphine (1.5 Kg) and benzoic acid (600 g) are dissolved in 6 L of THF, and to the resultant solution, is added a solution of 800 g of diethyl azodicarbonate in 1 L of THF. The mixture is stirred at room temperature for 15 hours, and reaction mixture is concentrated under reduced pressure. The concentrate is dissolved in warm hexane/THF and the mixture is extracted with water and a saturated NaCl solution. The organic phase is dried over magnesium sulfate and the solvent is distilled off under vacuum to provide a concentrate containing benzyl (2S, 3S, 5S) 5-benzoyloxy-2-hexyl-3-[(tetrahydro-2H-pyran-2-yl)oxy]-hexadecanoic acid ester which is used in the next step without purification.

EXAMPLE 11
Production of (2S, 3S, 5S) 5-Benzoyloxy-2-hexyl-3-[(tetrahydro-2H-pyran-2-yl)oxy]-hexadecanoic Acid The benzyl ester of Example 10 is dissolved in anhydrous 5 L of THF and HCl is added in an equimolar amount with respect to the benzyl ester. Under argon the ester is hydrogenated at room temperature for three hours by stirring the solution in the presence of Pd/C 10%. The solution is filtered and the catalyst is washed with THF, the washings are combined with the reaction mixture and the reaction mixture is neutralized with aqueous 1N NaOH. The organic layer is separated, dried over $MgSO_4$ and the solvent is evaporated under vacuum to provide a crude composition of(2S, 3S. 5S) 5-benzoyloxy-2-hexyl-3-[(tetrahydro-2H-pyran-2-yl)oxy]-hexadecanoic acid, which is used in the next step without further purification.

EXAMPLE 12
Production of (2S, 3S, 5S) 5-Benzoyloxy-2-hexyl-4-hydroxyhexadecanoic 1,3-lactone, i.e., (3S, 4S) 3-hexyl-4-[(S) 2-benzoyloxytridecyl]-2-oxetanone 500 g of the hexadecanoic acid of Example 11 is dissolved in 6 L of anhydrous ethanol and 30 g of toluene-4-sulfonic acid anhydride is added. The temperature of the reaction mixture is raised to 60° C. with stirring and maintained at 55–65° C. until the reaction is finished. The solvent is removed under vacuum and the residue is dissolved in warm hexane. The mixture is stirred for 2 hours cooled to −10° C. and allowed to stand overnight at 0° C. The crystals are removed from the solvent by filtration and washed with cold hexane to yield the compound (2S, 3S. 5S) 5-benzoyloxy-2-hexyl-4-hydroxyhexadecanoic 1,3 -lactone.

EXAMPLE 13
Production of (2S, 3S, 5S) 3,5-Dihydroxy-2-hexylhexadecanoic 1,3-lactone, i.e., (3S, 4S) 3-hexyl-4-[(S) 2-hydroxytridecyl]-2-oxetanone 200 g of the (2S, 3S, 5S) 5-benzoyloxy-2-hexyl-4-hydroxyhexadecanoic 1,3-lactone of Example 12 is suspended in a 4 L solution containing 0.01 N sodium hydroxide dissolved in a mixture of water-dioxane (1:1), and the resulting mixture is stirred at about 25° C. for about 12 hours to effect the hydrolysis of the benzoyloxy group to an alcohol group. The rection mixture is extracted 3 times with 2 L portions of hexane and the extracts are combined. After concentration of the extracts to dryness the solid is dissolved in warm hexane, cooled to 0° C. and stirred for 2 hours. The mixture is seeded with pure (2S, 3S, 5S) 3,5-dihydroxy-2-hexylhexadecanoic 1,3-lactone crystals and the mixture is allowed to sit overnight at 0° C. The crystals are filtered, washed with cold hexane and dried to produce about 125 g of (2S, 3S, 5S) 3,5-dihydroxy-2-hexylhexadecanoic 1,3-lactone, i.e., (3S, 4S) 3-hexyl-4-[(S) 2-hydroxytridecyl]-2-oxetanone.

EXAMPLE 14
Production of Ethyl 3,5-di-oxo-2-hexyl-hexadecanoate Ester

To a 20 L 3-neck flask equipped with a mechanical stirrer, argon inlet, reflux condenser, heating mantle and vacuum system, under argon is added a suspension 140 g of sodium hydride in 6 L of THF. The temperature is lowered to 0–5° C. and maintained as 1 Kg of methyl 2-acetyloctanoate (Aldrich 10887) is slowly added to this suspension with stirring. After one hour of stirring the mixture is cooled −10° C. and 1.25 Kg of 24% w/wn-Butyllithium (n-BuLi) (about 5 mol) in 3 L of hexane is added. After stirring at this temperature for 45 minutes, the flask is then cooled to below −15° C. followed by slowly adding 575 g of ethyl dodecanoate (Aldrich L4625). This solution is allowed to warm to −10° C. with stirring and is stirred at this temperature for 1 hour. The reaction solution is added under argon 1.25 L of 40% hydrochloric acid and 1.5 Kg of ice. The mixture is extracted twice with 5 L of hexane and water. The organic phases are combined, dried over magnesium sulfate, filtered, and the organic solvents are evaporated at reduced pressure to provide a solid residue (about 1.4 Kg).

EXAMPLE 15
Production of (3R, 5R) Ethyl 3,5-Di-hydroxy-2-hexyl-hexadecanoate Ester To a 20 L 3-neck flask equipped with a mechanical stirrer, argon inlet, reflux condenser, heating mantle, cooling apparatus, and vacuum system, under argon is added 8 mols (2.6 Kg) of (+)-β-chlorodiisopinocamphenylborane ("+-DIP-Cl"). To this was added 4 L of dry THF at room temperature over one hour. Once the mixture is dissolved together the temperature is lowered to −25° C. While maintaining the temperature between −20 and −25° C. the 1.4 Kg of ethyl 3,5-dioxo-tetradecanoate ester (Example 14) in 2 L of dry THF is slowly added with stirring (over a one hour period) to this solution. The reaction temperature is maintained between −10 and −20° C. for 8 hours and the reaction progress is monitored with HPLC. After the 8 hours, the temperature is allowed to gradually warm to about −5° C., and after 1 hour at this new temperature is allowed to warm to 0° C. in order to increase the rate of reaction. The reaction process is monitored by HPLC and the reaction is stopped after all the starting material is consumed. To the reaction mixture is slowly added 3 L of water (over a one hour period) while maintaining the reaction temperature below 1° C. About 4 L of methanol is then added, followed by 4 L of aqueous 5 M NaOH. The mixture is stirred at room temperature and the reaction is monitored by HPLC until it is complete (about two hours). The reaction mixture is allowed to separate and the aqueous layer is removed. The aqueous layer is extracted with hexane and the separated aqueous layer is neutralized with HCl, saturated with NaCl and extracted 3 times with 3×1 L of with warm hexane. The hexane layers are combined and concentrated by evaporation of the solvent at reduced pressure to provide a crude product which is dried over magnesium sulfate to provide about 1.3 Kg of solid.

EXAMPLE 16
Production of (4R, 6R) Tetrahydro-3-hexyl-4-hydroxy-6-undecyl-2H-pyran-2-one To a 20 L 3-neck flask equipped with a mechanical stirrer, argon inlet, reflux condenser, heating mantle and vacuum system, is charged under argon with 6 L of anhydrous toluene and the 1.3 Kg of product from Example 15 is slowly added to the solution with stirring pyridium para-toluenesulfonate and refluxed under argon for 2 hours to form the lactone. The reaction mixture is cooled to room temperature and washed twice with a saturated aqueous sodium carbonate solution. The organic phases are combined and evaporated under vacuum at about 40° C. to produce a product, and warm hexane is added to the product to dissolve it into a homogenous mixture. The warm hexane mixture is cooled to room temperature with stirring. The mixture is then cooled to −10° C. and stirred at that temperature for 15 hours. The crystalline solid is then filtered under suction. The filter cake is washed with cold hexane and dried over magnesium sulfate. The crystals are then dried overnight in a drier to remove any remaining solvent. About 1 Kg of (4R, 6R) tetrahydro-3-hexyl-4-hydroxy-6-undecyl-2H-pyran-2-one, having a m.p. of 95–96° C. is provided.

EXAMPLE 17

Production of (3S, 4S, 6R) Tetrahydro-4-benzoyloxy-3-hexyl-6-undecyl-2H-pyran-2-one A hydrogenator is purged twice with nitrogen and charged with the 1 Kg of product from Example 9 dissolved in 6 L of anhydrous ethyl acetate and 500 g of $PtO_2$ is added. The hydrogenator is purged twice with hydrogen and then charged with hydrogen at 50 bar. The temperature is raised to 40° C. and hydrogen flow is maintained at 50 bar for 12 hours. The catalyst is filtered off and the solution is evaporated. After dissolving in warm hexane, the product is cooled to 0° C. overnight and recrystallized to yield 900 g of (3S, 4S, 6R) tetrahydro-3-hexyl-4-hydroxy-6-undecyl-2H-pyran-2-one, having a m.p. of 108–1 09° C.

EXAMPLE 18

Production of (6S, 6R) 5,6 Dihydro-3-hexyl-6-undecyl-2H-pyran-2,4-dione

To a 20 L 3-neck flask equipped with a mechanical stirrer, argon inlet, reflux condenser, heating mantle and vacuum system, is charged under argon with 6 L of anhydrous acetone and 1 Kg of a (6S, 6R) racemic product prepared in a similar manner to the compound of Example 6, but from a (5R, 5S) racemic mixture of the compound described in Example 5. The temperature is lowered to about 20° C. and 1 L of Jones' reagent (chromic acid/conc. $H_2SO_4$ in acetone) is slowly added to the solution with stirring at an addition speed to maintain the temperature at less than 25° C. After addition of all of the Jones' reagent the mixture is stirred for 3 hours at 25° C. After completion of the reaction, the reaction mixture is poured into 15 L of $H_2O$. The lactone precipitates out and is filtered off. After dissolving filter cake in a warm ether/n-hexane solvent, the mixture is cooled and recrystallized to obtain 750 g of (6R) 5,6-dihydro-3-hexyl-6-undecyl-2H-pyran-2,4-dione, having a m.p. of 112.5–13.5° C.

EXAMPLE 19

Enzymatic Resolution of (6S, 6R) 5,6 Dihydro-3-hexyl-6-undecyl-2H-pyran-2,4-dione The compound of Example 18 is hydrogenated with Raney Nickil in substantially the same manner as the procedure of Example 7, and the 4 hydroxy group of the resulting compound is protected with a tetrahydro-2H-pyran-2-yl ether group substantially as described in Example 8. The lactone ring is opened substantially as described in Example 9, and the 5 R, 5S hydroxy group chirality is reversed with an ester group which is sufficiently polar to render the compounds soluble in a basic aqueous solvent by using shown the general procedures shown in Example 10. The benzyl alcohol group is removed from the acid group by hydrogenation as described in Example 11 and the resulting free acid 5S and 5R enantiomers are resolved in a basic aqueous medium by using a lipase such as PS 30, pig liver lipase and the like.

After 45 to 48% of the total 5 hydroxy esters have been cleaved (about 90% of the 5S compounds) by the lipase, the insoluble 5S hydroxy compounds are separated from the reaction mixture and washed with water. Also, the remaining reaction mixture is filtered to remove the lipase, and the lipase mass is washed with water which is added to the aqueous filtrate. The aqueous filtrate is set aside for further resolution.

The separated 5S hydroxy compounds, the aqueous insoluble portion are esterified with an excess of benzoic acid using the esterification procedures in an acidic $H_2SO_4$ and THF solvent. After completion of the esterification, the organic solution is washed with water, and separated from the aqueous layer. The procedures of Examples 11 and 12 are followed to yield the (2S, 3S, 5S) 3,5-dihydroxy-2-hexylhexadecanoic 1,3-lactone.

EXAMPLE 20

Recycling Filtrate Esters (greater than 90% 2R, 3R, 5R enantiomer) from the Lipase Separation The aqueous filtrate from Example 20 is obtained and stirred in 1N NaOH at 30° C. for 3 hours, neutralized with HCl and extracted with hexane. The hexane portions are combined and the solvent is evaporated. The procedures of Example 11 are followed to provide the compound (3R, 4R, 6R) 5,6-dihydro 3-hexyl-4-[(tetrahydro-2H-pyran-2-yl)oxy]-undecanyl-2H-pyran-2-one, which can be recycled through the processes of Examples 7–13 to produce a composition having greater than 90–95% of the yield the (2S, 3S, 5S) 3,5-dihydroxy-2-hexylhexadecanoic 1,3-lactone. Combining this 1,3 lactone product with the product of Example 19 provide a composition having greater than 95 to 97% of the (2S, 3S, 5S) 3,5-dihydroxy-2-hexylhexadecanoic 1,3-lactone.

EXAMPLE 21

10 grams of low viscosity chitosan (less than 500 cPs, readily available commercially, e.g., ChitoClear™ by Primex) which is greater than 95% deacylated chitin is dissolved in a 500 milliliter flask equipped with a stirrer thermometer and electrical heater, in a mixture of 190 g of dimethylsulfoxide and 10 g of paraformaldehyde, at 50° C. At this temperature, after the addition of 0.1 g of finely powdered sodium hydroxide, a solution of 1 g of 12-bromododecanoic acid ethyl ester in 10 g of dimethylsolfoxide is added over a period of about 30 minutes. The mixture is stirred for four hours at 50° C. The reaction mixture is cooled to room temperature, then poured into ethanol while the latter is being stirred vigorously. The solid is suction filtered, suspended repeatedly in ethanol until all the soluble substances are removed to yield a crude product. The crude product is stirred in an aqueous basic 1 N sodium hydroxide ethanol solution, which is then acidified with HCl until neutral pH for chitosan. The solid is washed twice with cold ethanol and cold water, and the solid is then dried to yield about 10 grams of ether functionalized chitosan. Analysis indicates that from 1% to 3% of the free hydroxyl groups on the chitosan polymeric backbone are etherified by the entry of the 12-dodecanoic acid group.

EXAMPLE 22

A colorless power of (2S, 3S, 5S) 3,5-dihydroxy-2-hexyl-hexadecanoic 1,3-lactone (6 g), produced as in Example 13 above (or as described on pages 11 and 12 of U.S. Pat. No. 4,202,824) is dissolved in 500 mL of THF to which is added Boc-(L) 2-amino-4-methylpentanoic acid chloride (3 g, Boc-(L)-Leucine). The reaction mixture is stirred and heated to reflux until HPLC indicates that the esterification is essentially complete. The organic phase is evaporated and the residue purified by chromatography on silica gel with toluene-ethyl acetate to yield 5-[Boc-(L) 2-amido-4-methylvaleryloxy]-2-hexyl-hexadecanoic 1,3-lactone (6 g).

EXAMPLE 23

The BOC group of the product (6 mg) of Example 2 is removed by hydrogenation at room temperature in 120 mL of THF in the presence of 10% Pd/C. After hydrogenation is completed, the catalyst is filtered off and the filtrate is evaporated to yield a crude free amino group product, which is taken up in 100 mL of THF. The functionalized chitosan product produced in Example 1 which has been converted to the acyl chloride derivative is taken up in 200 mL of THF and stirred while the crude free amino product is added dropwise at room temperature under argon. The mixture is gradually heated to 40° C. with stirring until HPLC indicates the formation of the carboxamide linked product. Yielded is 5-[2-{(4-chitosan methyl ether) benzoylamido}-4-methylvaleryloxy]-2-hexyl-hexadecanoic 1,3-lactone (about 15 grams).

EXAMPLE 24

A colorless power of (2S, 3S, 5S) 3,5-dihydroxy-2-hexyl-hexadecanoic 1 3-lactone (6 g), produced as in Example 13 above (or as described on pages 11 and 12 of U.S. Pat. No. 4,202,824) is dissolved in 500 mL of THF and 25 mL of anhydrous HCl to which is added the acyl chloride derivative of the compound of Example 21 (10 g). The reaction mixture is stirred and heated to reflux until HPLC indicates that the esterification is essentially complete. The organic phase is separated from the aqueous phase and the solvent is evaporated. The resulting product is washed with warm hexane and with water to provide funtionalized chitosan linked to the (2S, 3S, 5S) 3,5-dihydroxy-2-hexyl-hexadecanoic 1,3-lactone as an ester derivative of the 5S hydroxy group (15 g).

In view of the above description it is believed that one of ordinary skill can practice the invention. The examples given above are non-limiting in that one of ordinary skill in view of the above will readily envision other permutations and variations on the invention without departing from the principal concepts. Such permutations and variations are also within the scope of the present invention.

What is claimed is:

1. An intermediate compound according to the formula:

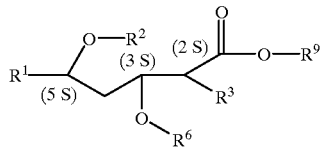

wherein:

$R^1$ and $R^3$ are each independently a $C_5$ to $C_{18}$ straight or branched alkyl chain which can be interrupted by 1 or 2 alkenyl double bonds, and $R^2$ is hydrogen or an alcohol protecting group $R^{10}$, wherein $R^{10}$ can be replaced by a hydrogen atom via ester hydrolysis or hydrogenation ether degradation, and $R^{10}$ is selectively removable with respect to the $R^6$ alcohol protecting group, and wherein $R^{10}$ is a member selected from the group consisting of tetrahydropyran, benzyl, t-butyldimethylsilyl and the like, $R^6$ is an alcohol protecting group that is selectively removable with respect to the $R^{10}$ group, wherein $R^6$ is selected from the group consisting of is selected from the group consisting of tetrahydropyran, benzyl, t-butyldimethylsilyl and the like, $R^9$ is H or an acid protecting group, such as a lower alkyl ester group, benzyl group and the like, or, a salt thereof.

2. A compound according to claim 1, wherein $R^1$ is undecyl and $R^3$ is hexyl or, a salt thereof.

3. A compound according to claim 2, wherein $R^2$ is a tetrahydropyranyl alcohol protecting group, $R^6$ is a benzyl protecting group and $R^9$ is a ethyl or benzyl group.

4. A compound according to claim 2, wherein $R^2$ is a benzyl alcohol protection group, $R^6$ tetrahydropyranyl alcohol protecting group and $R^9$ is a ethyl or benzyl group.

* * * * *